United States Patent [19]

Okabe

[11] Patent Number: 5,650,149

[45] Date of Patent: Jul. 22, 1997

[54] COSMETIC COMPOSITION FOR PROLIFERATING INDIGENOUS BACTERIA ON SKIN

[75] Inventor: Keiichiro Okabe, Tokyo, Japan

[73] Assignee: Kabushiki Kaisya Advance, Japan

[21] Appl. No.: 495,629

[22] PCT Filed: Dec. 14, 1994

[86] PCT No.: PCT/JP94/02093

§ 371 Date: Aug. 4, 1995

§ 102(e) Date: Aug. 4, 1995

[87] PCT Pub. No.: WO95/16431

PCT Pub. Date: Jun. 22, 1995

[30] Foreign Application Priority Data

Dec. 15, 1993 [JP] Japan .................... 5-342294

[51] Int. Cl.$^6$ ................. A61K 7/00; A61K 7/48
[52] U.S. Cl. ..................... 424/93.51; 424/195.1; 514/561; 514/762; 514/783; 514/844; 514/845; 514/846; 514/847; 514/848
[58] Field of Search ............... 424/93.51, 195.1; 514/561, 762, 783, 844, 845, 846, 847, 848

[56] References Cited

U.S. PATENT DOCUMENTS

| 4,454,159 | 6/1984 | Musher | 424/358 |
| 4,540,571 | 9/1985 | Schimanski | 424/81 |
| 4,883,659 | 11/1989 | Goodman et al. | 424/78 |
| 5,039,516 | 8/1991 | Goodman et al. | 424/59 |
| 5,073,545 | 12/1991 | Arima et al. | 514/27 |
| 5,086,040 | 2/1992 | Bonfils et al. | 514/8 |

FOREIGN PATENT DOCUMENTS

| 0 117 087 | 8/1984 | European Pat. Off. |
| 0 451 461 A2 | 10/1991 | European Pat. Off. |
| 2 604 624 | 8/1988 | France . |
| 4032972 A1 | 4/1991 | Germany . |
| 51-112587 | 10/1976 | Japan . |
| 4-91011 | 3/1992 | Japan . |
| 5-161471 | 6/1993 | Japan . |
| 2 165 151 | 4/1986 | United Kingdom . |

*Primary Examiner*—Nathan M. Nutter
*Attorney, Agent, or Firm*—Finnegan, Henderson, Farabow, Garrett & Dunner, L.L.P.

[57] ABSTRACT

A cosmetic composition containing triglyceride oleate and yeast extract and further, if desired, an L-cysteine hydrochloride as components for proliferating indigenous bacteria on the skin.

4 Claims, No Drawings

COSMETIC COMPOSITION FOR PROLIFERATING INDIGENOUS BACTERIA ON SKIN

TECHNICAL FIELD

The present invention relates to a cosmetic composition.

BACKGROUND ART

In the past, cosmetic compositions such as creams were composed so as to mimic as much as possible the skin protecting action, self-cleansing action, and other functions of the membranes of the human skin. The functions of conventional cosmetic compositions, however, have not been able to match the functions of the natural membranes of the skin.

SUMMARY OF THE INVENTION

Accordingly, the object of the present invention is to provide a cosmetic composition which further improves the skin protecting action, skin cleansing action, and other functions of conventional cosmetic compositions so as to give a coating of the skin close in function to the natural membranes of the skin.

In accordance with the present invention, there is provided a cosmetic composition comprising triglyceride oleate and yeast extract as components for proliferating the indigenous bacteria on the skin.

In accordance with the present invention, there is also provided a cosmetic composition further comprising as an ingredient for proliferating of the indigenous bacteria on the skin, in addition to the triglyceride oleate and yeast extract, an L-cysteine hydrochloride.

BEST MODE FOR CARRYING OUT THE INVENTION

In consideration of the fact that the skin protecting action, skin cleansing action, and other functions of conventional cosmetic compositions have not been sufficient if compared with the functions of the natural membranes of the skin, the present inventors took note of the fact that the natural membranes of the skin are the indigenous bacteria on the skin and their metabolites and, as a result, achieved the above-mentioned object by providing a cosmetic composition comprising components for proliferating the indigenous bacteria on the skin.

That is, the cosmetic composition according to the present invention includes triglyceride oleate and yeast extract, and further an L-cysteine hydrochloride, which are effective for proliferating Propinonibacterium acnes, Staphylococcus epidermidis, and other indigenous bacteria on the skin.

The ratios of addition of the above proliferating ingredients in the cosmetic composition (% by weight) depend on the compositions of the selective media for the skin indigenous bacteria (PUK medium; Kishishita, M., et al.: Appl. Environ. Microbiol., 40 1100–1105 (1980)) etc., but the preferable ranges are normally as follows:

0.03 to 50% by weight (more preferably 1 to 6% by weight) for triglyceride oleate;

0.5 to 30% by weight (more preferably 0.5 to 2% by weight) for yeast extract; and 0.01 to 0.1% by weight (more preferably 0.02 to 0.05% by weight) for the L-cysteine hydrochloride.

Further, these proliferating components are listed in the Japan Pharmacopoeia and the Standards of Cosmetic Ingredients, and therefore, the qualities, specifications, etc. are based on these standards. In particular, for the triglyceride oleate, olive oil containing 80 to 90% by weight thereof etc., may be used.

The cosmetic composition according to the present invention may contain therein any ingredients other than the above-mentioned components within a range not adversely affecting the effects of the present invention. For example, it is possible to suitably formulate with purified water, ethanol, oily substances, humectants, thickeners, antiseptics, emulsifying agents, medicinal ingredients, powders, fragrants, emulsion stabilizers, pH adjusters, etc.

More specifically, as the oily ingredients, liquid paraffin, vaseline, paraffin wax, squalane, beeswax, carnauba wax, olive oil, lanolin, higher alcohols, fatty acids, synthetic ester oils derived from higher alcohols and fatty acids, silicone oil, etc., can be exemplified.

As the humectants, sorbitol, xylitol, glycerol, maltose, propylene glycol, 1,3-butylene glycol, 1,4-butylene glycol, sodium pyrrolidone carboxylate, lactic acid, sodium lactate, polyoxypropylene fatty acid esters, polyethylene glycol, etc., can be exemplified.

As the thickeners, electrolytes such as carboxyvinyl polymers, carboxymethylcellulose, polyvinyl alcohol, carrageenan, gelatin, and other water soluble polymers and sodium chloride, potassium chloride can be exemplified.

As the antiseptics, methylparaben, ethylparaben, propylparaben, butylparaben, sodium benzoate, etc., can be exemplified.

As the emulsifying agents, nonionic surfactants such as polyoxyethylene alkyl ethers, poloxyethylene fatty acid esters, polyoxyethylene sorbitan fatty acid esters, glycerol fatty acid esters, polyglycerine fatty acid esters, poloxyethyleneglycerine fatty acid esters, polyoxyethylene hydrogenated castor oil can be exemplified.

As the powders, talc, sericite, kaolin, silica, bentonite, vermiculite, zinc oxide, mica, titanated mica, titanium chloride, magnesium chloride, zirconium chloride, barium sulfate, red ion oxide, iron oxide, ultramarine, etc., can be exemplified.

As the pH adjusters, buffer agents such as lactic acid-sodium lactate, citric acid-sodium citrate can be exemplified.

As the various other effective ingredients, it is possible to add allantoin, vitamin E derivatives, glycyrrhizin, ascorbic acid derivatives, kojic acid, arbutin, pantothenic acid derivatives, placenta extract, antiphlogistics, coix seed, and various plant extracts so as to improve the melanine suppressing effect.

Further, according to the present invention, it is possible to add various UV absorbants so as to provide a cosmetic composition which features both a sunburn preventing effect and treatment effect.

The cosmetic composition according to the present invention can provide a sebaceous coating (including indigenous bacteria) close to the natural state, and therefore, can achieve an excellent skin protecting action and self-cleansing action. Further, in general, the amount used is preferably, in the case of, for example, a cream like or ointment like preparation, 1 to 20 mg per square cm of skin surface and, in the case of a liquid preparation, 1 to 10 mg per square cm of skin surface, but the present invention is not limited to these.

EXAMPLES

The present invention will be explained in further detail by the following Examples, but the present invention is by no means limited to these Examples.

|  | (wt %) |
| --- | --- |
| (Formula 1 (Cosmetic Water)) | |
| Glycerol | 4 |
| Polyoxyethylene hydrogenated castor oil | 1.5 |
| Ethanol | 10 |
| Sodium pyrrolidone carboxylate | 2 |
| Fragrant | q.s. |
| Olive oil (triglyceride oleate 85%) | 5 |
| Yeast extract | 0.6 |
| (L-cysteine hydrochloride) | 0.03 |
| Purified water | Balance 100 |
| Formula 2 (Cream) | |
| Vaseline | 4 |
| Cholesterol | 0.6 |
| Cetanol | 0.5 |
| Sorbitan sesquioleate | 2 |
| Liquid paraffin | 4 |
| Squalane | 10 |
| Solid paraffin | 4 |
| Butylparaben | 0.1 |
| Methylparaben | 0.1 |
| Perfume | 0.2 |
| Olive oil (triglyceride oleate) | 15 |
| Yeast extract | 1.5 |
| (L-cysteine hydrochloride) | 0.05 |
| Purified water | Balance 100 |

Test Example 1

For each of the above formulae (using as controls those with the proliferating components removed), 0.2 ml thereof was uniformly spread and allowed to be absorbed on a basic agar medium ($\Phi$3.5 cm Petri dish: PUK medium from which yeast extract, cysteine hydrochloride, and sodium oleate were removed and including 1.5% trypticase (BBC), 0.5% heart extract (Nissui), 1% glycerol, 0.2% sodium chloride, 0.2% $K_2HPO_4$, 0.002% Bromocresol purple, 1.5% agar, pH 6.8, 3 ml). Then, a diluted suspension of the indigenous bacteria taken from the skin of the forehead of a healthy subject was applied, anaerobic culture was performed, and the state of growth of the colonies of bacteria was compared and studied by count and size.

The sampling of the skin indigenous bacteria was effected by the method of strongly rubbing 20 times a 1 $cm^2$ location of the forehead by a sterile cotton swab moistened with physiological saline, then causing the bacteria to be suspended in a diluent (0.5% $KH_2PO_4$, 0.4% $Na_2HPO_4$, 0.1% Tween 80, 0.03% cysteine hydrochloride, pH 6.8, 2 ml). The bacterial suspension was further diluted two stages by the 10-fold dilution method. An aliqute of 0.05 ml of each dilution was spread on the above mentioned agar medium plate and anaerobic grobe culture (10% $CO_2$, 90% $N_2$, 10% $H_2$, steel wool method) was performed at 37° C. for 4 days.

In the controls having no proliferating components, no substantial amounts of colonies were observed. The samples having the colonies exhibited a proliferation corresponding to $10^4$ to $10^5$ $cfu/cm^2$ (per skin area). Further, the samples further having an L-cysteine hydrochloride gave colonies about 1.5 times larger, but substantially the same in number. These colonies were uniform in appearance. A randomly selected 20 strains thereof were hooked by sterile loops and streaked on two GAM plate agar media. These strains were cultured aerobically and anaerobically (37° C., 3 to 7 days). All were anaerobic bacteria. From inspection of the biochemical characteristics (Bergy's Manual), all were Propionibacterium acnes of the Propionibacterium genus. In parallel with this, the diluted suspensions of the bacteria sampled from the skin mentioned above were applied to various isolation plate media (tryptosoy agar medium, mannite sodium chloride agar medium (Nissui Seiyaku), potato dextrose agar medium (Nissui Seiyaku) and aerobically cultured (37° C., 3 to 7 days), whereupon the grown colonies were all identified as the Staphylococcus epidermidis of the Staphylococcus genus. The count was only approximately from $10^2$ to $10^3$ $cfu/cm^2$ (per skin area). As is clear from the above results, a proliferating promoting effect of triglyceride oleate, yeast extract, and L-cysteine hydrochloride on the growth of the Propionibacterium genus, the most dominant indigenous bacteria on the skin can be shown by the properties of the test method.

Test Example 2

To further study the above indigenous bacteria proliferating factors, three standard strains of Propionibacterium aches and Staphylococcus epidermidis, which are dominant indigenous bacteria of the healthy skin, and further Staphylococcus aureus, which is the dominant indigenous bacteria of locations of atopic dermatitus, were selected and subjected to three types of mixed culture in the presence of yeast extract and a cysteine hydrochloride under conditions of relatively good enrichment, and the effect of the addition of olive oil (triglyceride oleate) on the proliferation of each bacteria was observed.

For the standard strains, Propionibacterium acnes ATCC11827, Staphylococcus epidermidis IAM 12012, and Staphylococcus aureus IID671 were used. For the basal medium, GAM broth medium (1% peptone, 0.3% soybean peptone, 1% protease peptone, 1.35% digested serum powder, 0.5% yeast extract, 0.22% broth extract, 0.12% liver extract powder, 0.3% dextrose, 0.25% $KH_2PO_4$, 0.3% NaCl, 0.5% soluble starch, 0.03% L-cysteine hydrochloride, 0.03% sodium thioglycolate, pH 7.3). The triglyceride oleate used was reagent use olive oil specific for measurement of lipase (Nakarai Kagaku Yakuhin) of a final concentration of 0.03%.

The single strain of Propionibacterium acnes was anaerobically cultured at 37° C., but aerobic stationary culture was used for the mixed culture of the Staphylococcus epidermidis and Staphylococcus aureus. The preculture of the latter two strains was performed aerobically. The live bacteria count was measured using ordinary agar containing 0.2% dextrose. The Staphylococcus epidermidis and the Staphylococcus aureus were aerobically cultured at 37° C. for one day after which the white colonies were counted as the former and the yellow colonies as the latter.

The Propionibacterium acnes was anaerobically cultured at 37° C. for 4 days, then was aerobically cultured for a further 2 to 3 days, then the grayish-white, small, lustrous ridged colonies were selectively counted. The basal control medium and the olive oil addition test medium were respectively inoculated with 3.3% of the preculture solution of Propionibacterium acnes which had been anaerobically cultured for 24 hours and 0.33% of the precultured solution of Staphylococcus epidermidis and Staphylococcus aureus which had been aerobically cultured for 18 hours. The living bacteria counts were measured after culturing for 0, 7, and 24 hours.

As shown in Table 1, the effects of addition of olive oil on the proliferation of the bacteria at the mixed cultivation of the three strains of skin indigenous bacteria appeared up to 7 hours after culturing. Propionibacterium acnes and Staphylococcus epidermidis tended to be slightly promoted in proliferation, while Staphylococcus aureus tended to be somewhat inhibited in growth. When the culture was further continued, the effect of the addition almost completely disappeared for the former two strains, but the latter was observed to be further largely inhibited in proliferation.

The above results suggest that olive oil, which serves as a growth promoting factor for indigenous bacteria on the skin even in media with sufficient enrichment conditions simultaneously has the effect of normalizing skin, that is, inhibiting the growth of Staphylococcus aureus, which is known as an atopy aggravating factor.

TABLE 1

Effect of Addition of Olive Oil on Proliferation of Bacteria in Mixed Culture of Three Strains of Skin Indigenous Bacteria (in Basal Medium Containing Yeast Extract and L-Cysteine Hydrochloric Acid Salt)

| Name of bacteria | Oil (%) | Living Bacteria count (count/ml) | | | Proliferation constant ($\mu$) | Effect of addition of olive oil (+)/(−) |
|---|---|---|---|---|---|---|
| | | 0 hour | 7 hours | 24 hours | | |
| S. epidermidis | 0.00 | 6.3 | 7.3 | 7.9 | 0.33 | Growth promoted |
| | 0.03 | 6.3 | 7.7 | 7.9 | 0.46 | 1.40 |
| P. acnes | 0.00 | 7.9 | 8.5 | 8.8 | 0.20 | Growth promoted |
| | 0.03 | 7.9 | 8.6 | 8.9 | 0.23 | 1.15 |
| S. aureus | 0.00 | 6.2 | 8.6 | 8.9 | 0.79 | Growth promoted |
| | 0.03 | 6.2 | 8.4 | 8.0 | 0.72 | 0.91 |

*Proliferation constant ($\mu$) = (2.303 × (logN$_{t=7}$logN$_{t=0}$))/(T$_7$–T$_0$) (where, N: living bacteria count and T, t = hours of culture)

Test Example 3

The effect on the indigenous bacteria flora of the face (forehead) and skin when cosmetic water and cosmetic cream containing these indigenous bacteria proliferating factors were actually used continuously by test subjects every morning after washing their faces was observed. Four healthy female volunteers (25 to 43 years old) were selected as test subjects. Bacteria was taken from their foreheads in the same way as in Test Example 1 and the flora analyzed over 4 weeks. In parallel with this, skin oil was sampled by an absorbent cotton swab from the areas adjoining those where the bacteria were taken and the suspended fatty acids were analyzed by gas chromatography. Table 2 shows the results regarding the trends in the count of the skin indigenous bacteria along with use of a cosmetic cream.

Almost no increase was observed in the total bacteria count after the start of use. A look at the most dominant bacteria, Propionibacterium aches, shows that there was an average 2.5- to 3-fold increase, but this was within the normal range of change on the skin of healthy subjects and cannot be said to have been abnormal proliferation.

Further, the next dominant Staphylococcus epidermidis accounted for about 1/10 of the amount of the most dominant bacteria and increased 2- to 4-fold on an average after use of the cosmetic. This was also within the range of variation of the skin of average healthy subjects and was not abnormal proliferation. In this test, there was substantially no other skin indigenous bacteria detected on the selective plate medium, including Staphylococcus aureus.

Table 3 shows the changes in the composition of the free fatty acids caused by use of the cream. The average value of the total free fatty acids sampled was 0.6 to 0.5 µg per cm$^2$—no change. The ratio of the different suspended fatty acids in the total amount of suspended fatty acids after use fell somewhat in the case of lauric acid (C12:0) and increased slightly in the case of oleic acid (C18:1) and palmitoleic acid (C16:1). However, it is these minor changes that are indicators of the lipase activity of the proliferating indigenous bacteria. The evaluation can be made that the bacteria were contributing positively to maintaining the balance of the ecosystem present between the indigenous bacteria flora and skin in the formation of the sebaceous membrane.

TABLE 2

Trends in Count of Skin Indigenous Bacteria Along With Use of Cosmetic Water and Cosmetic Cream (Average Value of Test Subjects: 4 Healthy Females, Ages 27 to 43)

| Bacteria | Number of detected colonies (cfu/cm$^2$) | | |
|---|---|---|---|
| | Before use | 2 weeks after use | 4 weeks after use |
| Bacteria count | 1.3 × 10$^6$ | 2.0 × 10$^6$ | 2.5 × 10$^6$ |
| P. acnes | 0.8 × 10$^6$ | 2.0 × 10$^6$ | 2.5 × 10$^6$ |
| P. granulosum | Below limit of detection | Below limit of detection | Below limit of detection |
| S. epidermidis | 1.1 × 10$^4$ | 1.9 × 10$^4$ | 4.0 × 10$^4$ |
| S. capitis | 1.5 × 10$^3$ | 0.3 × 10$^3$ | 0.1 × 10$^3$ |
| S. aureus | Below limit of detection | Below limit of detection | Below limit of detection |
| Micrococcus | Below limit of detection | Below limit of detection | Below limit of detection |
| Streptococcus | Below limit of detection | Below limit of detection | Below limit of detection |
| Bacillus | Below limit of detection | Below limit of detection | Below limit of detection |
| Yeast | Below limit of detection | Below limit of detection | Below limit of detection |

(Note) "Below limit of detection": <1 × 10$^2$.

TABLE 3

Trends in Free Fatty Acids on Epidermis Along With Use of Cosmetic Water and Cosmetic Cream (Average Value of Test Subjects: 4 Healthy Females)

| Epidermis free fatty acids | Percent of free fatty acids | | |
|---|---|---|---|
| | Before use of cream | 2 weeks after use | 4 weeks after use |
| Total free fatty acids | 100% | 100% | 100% |
| Lauric acid (C12:0) | 12 | 5 | 3 |
| Myristic acid (C14:0) | 8 | 8 | 7 |
| Palmitic acid (C16:0) | 31 | 36 | 33 |
| Palmitoleic acid (C16:1) | 10 | 14 | 14 |
| Stearic acid (C18:0) | 13 | 13 | 11 |
| Oleic acid (C18:1) | 10 | 15 | 13 |
| Linolic acid (C18:2) | 1 | 1 | 1 |
| Linolenic acid (C18:3 | — | — | — |
| Alginic acid (C20.0) | — | 3 | — |
| Arachidonic acid (C20:4) | 15 | 5 | 17 |

INDUSTRIAL APPLICABILITY

The cosmetic composition of the present invention promotes the proliferation of indigenous skin bacteria, and therefore, has the effect of providing a sebaceous coating layer closer to the natural state.

I claim:

1. A cosmetic composition for application to the skin of a user and effective for proliferating indigenous bacteria on the skin, said cosmetic composition comprising, based on the weight of the cosmetic composition, (a) from 0.03 to 50% by weight of triglyceride oleate and, (b) from 0.5 to 2% by weight of yeast extract.

2. The cosmetic composition of claim 1, further comprising (c) from 0.02 to 0.05% by weight of an L-cysteine hydrochloride as a proliferating component.

3. The cosmetic compositon of claim 1, further comprising one or more ingredients selected from the group consisting of water, ethanol, oily substances, humectants, thickeners, antiseptics, emulsifying agents, medicinals, powders, fragrants, emulsion stabilizers and pH adjusters, and being in the form of a cream or ointment.

4. The cosmetic composition of claim 2, further comprising one or more ingredients selected from the group consisting of water, ethanol, oily substances, humectants, thickeners, antiseptics, emulsifying agents, medicinals, powders, fragrants, emulsion stabilizers and pH adjusters, and being in the form of a cream or ointment.

* * * * *